(12) United States Patent
van Loon (10) Patent No.: US 6,951,650 B1
(45) Date of Patent: Oct. 4, 2005

(54) ANTIGENIC CLASS OF AVIAN REOVIRUSES

(75) Inventor: Adriaan Anthonius Wilhelmus Maria van Loon, Sambeek (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/493,484

(22) Filed: Jan. 28, 2000

(30) Foreign Application Priority Data

Jan. 29, 1999 (EP) ........................................... 99200259

(51) Int. Cl.[7] ............................................... A61K 39/15
(52) U.S. Cl. .................................................. 424/215.1
(58) Field of Search .......................... 424/215.1, 159.1, 424/184.1, 146.1

(56) References Cited

FOREIGN PATENT DOCUMENTS

| | | | |
|---|---|---|---|
| EP | 0 101 348 A | | 2/1984 |
| EP | 0 101 348 | * | 2/1984 |
| EP | 0 687 728 A | | 12/1995 |
| EP | 0 687 728 A2 | * | 12/1995 |

OTHER PUBLICATIONS

Avian reovirus infections. Jones R C. Revue Scientifique et Technique, (Aug. 2000) 19(2):614–25.*

Generation and genetic characterization of avian reovirus temperature–sensitive mutants. Patrick M; Duncan R; Coombs K M. VIROLOGY, (May 25, 2001) 284 (1):113–22.*

Antigenic comparisons of selected avian reoviruses by use of the plaque–reduction neutralization assay. Nersessian B N; Lukert P D; Goodwin M A. American Journal of Veterinary Research, (Sep. 1989) 50(9):1475–80.*

In vitro and in vivo characterization of avian reoviruses. I. Pathogenicity and antigenic relatedness of several avian reovirus isolates. Rosenberger J K; Sterner F J; Botts S; Lee K P; Margolin A. Avian Diseases, (Jul.–Sep. 1989) 33(3):535–44.*

Sequence analysis of the S3 gene from a turkey reovirus. Kapczynski Darrell R; Sellers Holly S; Simmons Valrie; Schultz–Cherry Stacey. Virus Genes, (2002) 25(1):95–100.*

M.R.Rekik et al: "Serlogical and Pathoenic Characterization of Avian Reoviruses Isolated in Quebec". vol. 93, No. 4 (Abstract only).

L. Van Der Heide: "Viral Arthritis/Tenosynovitis: A review avian pathology", vol. 6, 1977, pp. 271–284.

* cited by examiner

*Primary Examiner*—Jeffrey S. Parkin
(74) *Attorney, Agent, or Firm*—William P. Ramey, III

(57) ABSTRACT

The present invention provides a new antigenic class of avian reoviruses which are involved in enteric disease conditions in poultry. Moreover, the invention provides a vaccine for use in the protection of poultry against such disease conditions derived from the new type of avian reoviruses.

10 Claims, 3 Drawing Sheets

Figure 1a (Corrected)

Figure 1b (Corrected)

Figure 2a (Corrected)

Figure 2b (Corrected)

Figure 3a (Corrected)

Figure 3b (Corrected)

ANTIGENIC CLASS OF AVIAN REOVIRUSES

FIELD OF THE INVENTION

The present invention relates to an avian reovirus and a vaccine comprising an avian reovirus in a live attenuated or inactivated form.

BACKGROUND OF THE INVENTION

Commercial broiler production evolved over the last several decades into an industry which is characterised by its high efficiency in the confinement rearing of the livestock. However, the strong tendency towards increasing of the efficiency of the rearing phase is not accomplished without encountering some inherent difficulties. Most notable is the increased incidence of infectious diseases that often occurs in high density, close confined animal populations. Many of the most devastating diseases in poultry have been limited or controlled by vaccination or by treatment with therapeutic agents such as antibiotics. Unfortunately, however, there are still a number of diseases of complex aetiology that have not been controlled with drugs and for which a suitable vaccination program is unavailable.

Since the late 1970s, the poultry industry has been confronted with such complex diseases in broiler chickens suffering from enteric problems. One of such diseases which results in a variety of disease conditions in affected chickens, including enteritis, is named for the main clinical sign and macroscopical observation: malabsorption syndrome (MAS). Alternatively, this disease is designated as infectious runting stunting syndrome, pale bird disease or brittle bone disease. Although a large number of assorted disease conditions are linked with MAS, in all cases poor growth and retarded feathering are observed. Additionally, a large variety of other signs and lesions, such as mortality, secretion of too liquid faeces and/or maldigested feed, pancreatic atrophy, proventriculitis, bone changes, thymic and bursal atrophy, etc. have been correlated with MAS.
Kouwenhoven et al. (Avian Pathology, 17, 879–892, 1988) defined MAS by five criteria, i.e.
(i) growth impairment up to 3 weeks after infection of one-day-old chicks
(ii) excretion of yellow orange mucoid to wet droppings
(iii) increased plasma alkaline phosphatase (ALP) activity
(iv) decreased plasma carotenoid concentration (PCC)
(v) macroscopically widened epiphyseal growth plates of the proximal tibia.

Retarded growth in broilers becomes obvious by 1 week of age or earlier. From 5 to 20% of the birds in a flock may be affected and these birds will be half the size or less of their penmates by 4 weeks of age. Affected flocks have poor feed conversions and the intestines are pale and contain undigested feed.

Although the pathogenesis of MAS is poorly understood, the likely pathogenesis of this syndrome is the direct action of infectious agent(s) on the digestive tract and associated organs, which would also explain the recurring secretion of too liquid faeces and/or maldigested feed.

The syndrome described here results in a general lack of performance, including diminished weight gains, poor feed conversion and reduced marketability of the affected flocks. As a result of MAS the poultry industry suffers major economical losses annually. Therefore, the poultry industry is in need for a way to control MAS, such that one or more of the assorted disease conditions observed in broilers can be prevented.

Reoviruses are ubiquitous in poultry world-wide. Reoviruses have been found to be the causative agent of an arthritic condition affecting the major weight bearing joint capsules and tendon sheets in the legs, designated as viral arthritis/tenosynovitis.

In some reports reoviruses were also isolated from chickens displaying MAS associated disease condition. In these reports it is speculated that the reoviruses have an etiological relationship with one or more of the MAS associated disease conditions, but firm proof of the involvement of reoviruses in MAS was not provided therein.

In van der Heide et al. (Avian Diseases 25, 847–856, 1981) a reovirus was isolated from the intestines of young broilers with clinical diarrhoea. Although this reovirus isolate was capable of inducing lesions of tenosynovitis and femoral head fractures and osteoporosis, this isolate did not consistently induce diarrhoea in chickens experimentally infected with the reovirus.

Page et al. (Avian Diseases 26, 618–624, 1982) isolated reoviruses from a flock experiencing lameness, stunting and erratic feather development. Although, the oral inoculation into susceptible broiler-type chickens produce a clear effect on weight gains, feather development and induced lesions in a number of organs, the induction of diarrhoea or wet letter was not reported.

Hieronymus et al. (Avian Diseases 27, 246–254, 1983) reported the isolation of several strains of reovirus from the intestines of chickens with suspected MAS and determined the antigenic relationship of these strains with reovirus strain S1133 which is commonly used as a vaccine strain for the control of infectious tenosynovitis. The authors confirm that despite the fact that the reoviruses were isolated from chickens with clinical MAS, it remained to be proven that the reoviruses were the causative agent of MAS.

Eidson et al. (Poultry Science 64, 2081–2086, 1985) investigated the effect of an inactivated reovirus vaccine, derived from the C08 strain isolated by Hieronymus et al., in broiler flocks experiencing problems with MAS as well as tenosynovitis. Although the vaccine had a positive effect on body weight of the broiler population, there was no difference in feed conversion observed. Furthermore, no effect of the vaccine on enteritis-associated disease conditions, such as wet litter was reported.

Rosenberger et al. (Avian Diseases 33, 535–544, 1989) also isolated several reovirus strains from the tendons and bone marrow of field-reared commercial broiler chickens. Although, chickens inoculated with the reovirus strains were examined for clinical disease, signs of diarrhoea or wet litter were not reported.

Kouwenhoven et al. (Avian Pathology 17, 879–892, 1988) also investigated the role of reovirus in the malabsorption syndrome. These authors could not reproduce MAS with reovirus isolated from a field case, and concluded that reovirus is not the primary etiological agent of MAS. It is speculated therein that infectious agents, including reoviruses and adenoviruses may act as some kind of trigger in the malabsorption syndrome.

However, in addition to the above-mentioned publications, many other viruses have been associated with MAS. These include rotaviruses, parvoviruses, enterovirus-like viruses, togarvirus-like viruses, coronavirus-like viruses, adenoviruses and caliciviruses. Additionally, it was also suggested that bacteria be involved in the aetiology. MAS-like field syndromes have also been attributed to mycotoxins in the prior art and it is speculated that mycotoxins or other toxins should not be ignored as the causative agent of MAS.

In a recently published review (World Poultry 14, 57–58, 1998), McNulty summarised the state of the art on MAS. McNulty stressed the non-availablity of a vaccine against MAC and stated that the virus isolations, as well as the virologic and microbiologic examinations of samples isolated from the field reported so far have not provided useful results with regard to the identification of the causative agent(s) of MAS. McNulty speculated that this approach is not likely to yield useful results. Instead, management measures in MAS affected production sites is considered to be the best weapon for control of MAS.

Hence, there still exists a need for a vaccine which induces an effective protection against certain enteric problems experienced by chickens, such as the enteric problems associated with MAS, resulting in the secretion of too liquid faeces and/or maldigested feed.

Moreover, avian reoviruses display considerable antigenic heterogeneity and the emerging of new antigenic classes of avian reoviruses may have important implications for the use of reovirus vaccines in poultry.

SUMMARY OF THE INVENTION

The present inventors have now identified a novel antigenic class of avian reoviruses. Furthermore, it is demonstrated that avian reoviruses belonging to this novel antigenic class are able to induce pronounced disease conditions which are also associated with MAS, such as secretion of too liquid faeces and/or maldigested feed and growth retardation.

Therefore, it is an object of the present invention to provide the causative agent of a MAS-like enteric disease condition belonging to a new antigenic class of avian reoviruses.

Another object of the present invention is to provide a vaccine which effectively affords protection in poultry against disease caused by avian reoviruses of the new antigenic class.

It is a further object of the present invention to provide a vaccine which effectively affords protection in poultry against an enteric disease condition which is also associated with MAS.

DETAILED DESCRIPTION OF THE INVENTION

It has not been found that these objects can be met by providing an avian reovirus belonging to an antigenic class of avian reoviruses, characterised in that the avian reovirus belonging to the antigenic class is able to induce antiserum in an animal, which antiserum causes a reduction of the plaques formed by avian reovirus ERS, a sample of which is deposited at the ECACC, Salisbury, UK under accession no. 99011475, of at least 75% in a plaque reduction assay.

It has been observed that such avian reoviruses not only display hitherto unknown antigenic properties (Example 1, Table 2 and 3), but it has also been found that the avian reoviruses according to the present invention are able to induce the secretion of too liquid faeces and/or maldigested feed by a broiler chicken or in some cases may even lead to mortality. Hence the new avian reovirus is designated herein as enteric reovirus strain (ERS).

The excretion of wet faces in broiler flocks is one of the disease conditions which is also generally observed in MAS affected broilers in the field. Moreover, it is anticipated that this clinical disease condition is one of the causes of the most pronounced clinical signal in MAS affect broiler, i.e. that of growth retardation. In the examples it is shown that an avian reovirus according to the invention induces the excretion of wet faeces by broilers orally infected with the reovirus, i.e. around the cloaca of the birds clothing of pasting was observable.

The experiments in the examples also show that the oral infection of the new avian reovirus also results in a growth retardation in the infected broilers if compared with the control chickens.

The plaque reduction assay is an assay which is widely used in the art for determining the antigenic relationship between (avian reo)virus isolates (see e.g. Nersessian et al., Am. J. Vet Res. 50, 1475–1480, 1989). Moreover, for the purpose of the present invention a detailed description of the plaque reduction assay is provided in Example 1. Obviously, the antiserum to be used in the plaque reduction assay should be of appropriate quality. Methods for the preparation of such antiserum are also described in Example 1.

Generally, appropriate antiserum raised against live avian reoviruses can be prepared by inoculating 3 to 4 weeks old SF chickens subcutaneously or intramuscularly with a live virus strain having an infectious titre between $10^{2.0}$–$10^{9.0}$ TCID50/animal; more preferably between $10^{3.0}$ $10^{6.0}$ TCID50/animal. Blood can be collected 3 to 4 weeks after infection, preferably 4 weeks after infection. Chickens may also be re-infected with the same live virus strain 3 to 4 weeks after the first infection with approximately the same dose as used in the first infection. Blood is collected between 2 and 4 weeks after the second infection. Appropriate antiserum raised against inactivated avian reovirus strains can be obtained by inoculating 3 to 4 weeks old SPF chickens subcutaneously or intramuscularly with the inactivated virus preparation. The infectious titre of the preparation before inactivation may be between $10^{7.0}$–$10^{11.0}$ TCID50l /animal; more preferably between $10^{8.0}$–$10^{10.0}$ TCID50/animal. Blood can be collected 3to 4 weeks after inoculation, preferably 4 weeks after inoculation. Chickens may also be re-inoculated with the same inactivated virus preparation 3 to 6 weeks after the first inoculation. Blood is collected between 2 and 4 weeks after the second inoculation.

The identification of the novel avian reovirus according to the invention allows the preparation of new avian reovirus vaccines which can effectively protect poultry against disease conditions resulting from the infection by the new antigenic class of avian reoviruses. In particular, the novel avian reoviruses allow the preparation of new avian reovirus vaccines which can effectively protect poultry against disease conditions such as the secretion of too liquid faeces and/or maldigested feed and growth retardation. Such disease conditions are also associated with MAS.

The avian reovirus according to the invention can also be isolated from the field. An important aspect of the method of isolation is the identification of the target animal to be used as a starting-point for the virus isolation. A typical broiler to be used for this purpose shows the following signs: the secretion of too liquid faeces and/or maldigested feed resulting in growth retardation.

Subsequently, the intestine is isolated from the affected chicken followed by homogenisation of the organ in a suitable buffer. Thereafter, the homogenises tissue is centrifuged and the supernatant is filtrated through filters with a pore size of 0.2 μm. A sample of the filtrate is added to freshly prepared primary chicken cells, preferably chicken embryo liver (CEL) cells, and 4–8 days after incubation the monolayers are inspected for the presence of a cytopathic effect (CPE). If no CPE is present a freeze/thawed suspension of the first monolayer is added to freshly prepared CEL cells. If after the first passage or the second passage CPE is observed, then the virus is further characterised by its in vivo properties in broilers to induce the secretion of too liquid faeces and/or maldigested feed and by its antigenic properties as determined in the plaque reduction assay or immunofluorescence-technique (IFT) using specific polyclonal— and monoclonal antibodies as described below. A more detailed method for the isolation of an avian reovirus according to the present invention is disclosed in Example 1.

Although the intestines are used in the process for the isolation of the present avian reovirus as the preferred starting material, the avian reovirus can also be isolated from the liver of affected broiler chickens or from the faeces excreted by such a broiler chicken. It should also not be excluded that other organs may serve as the starting material for the isolation of the avian reovirus according to the invention.

In particular, the present invention provides an avian reovirus as described above, the induced antiserum against the avian reovirus being able to cause a reduction of the plaques formed by avian reovirus ERS, a sample of which is deposited at the ECACC, Salisbury, UK under accession no. 99011475, of at least 80%, preferably at least 90%, in a plaque reduction assay.

In an even more preferred embodiment of the invention an avian reovirus is provided which displays a specific immunological reaction pattern with a specific panel of polyclonal antiserum and monoclonal antibodies (Moabs). This specific reaction pattern is different from that displayed by hitherto known avian reoviruses.

Monoclonal antibodies are useful for identifying characteristics of an infectious agent, and for determining similarities and differences among different isolates of the same or similar micro-organism. Vakharia et al. (Proceedings of the International Symposium on adenovirus and reovirus infections in poultry, Rauischholzhausen, Germany, 1996, 295–304) disclosed a panel of 9 anti-reovirus Moabs and tested avian reovirus field isolates for their reactivity with these Moabs. Different patterns of reactivity of the panel of Moabs allowed the classification of the isolated based on its relatedness to the pattern of reactivity.

In this embodiment of the invention an avian reovirus as described above is provided which is further characterised by (i) its reactivity in the IFT with a polyclonal antiserum raised against an avian reovirus isolate, preferably against the prototype reovirus strain 1133, and (ii) the absence of reactivity in the IFT with the Moabs INT 13-06, INT 14-11 and 15-01 INT (samples of which are deposited at the ECACC under accession no. 99011472, 99011473 and 99011474, respectively).

The avian reovirus according to the invention defined by the panel-pattern represents a novel antigenic type of reoviruses as demonstrated in Example 1 and Table 3. Despite the fact that many of the prior art reovirus strains shown in Table 3 are isolated from tissues of broiler chickens (including intestines) showing signs and lesions associated with MAS, avian reoviruses according to the present invention having the novel antigenic properties defined above have not been disclosed in the prior art.

An even more preferred avian reovirus according to the present invention is avian reovirus ERS (isolate 1) which is characteristic for avian reoviruses according to the present invention, a sample of which is deposited at the ECACC under accession no. 99011475.

The avian reovirus according to the invention can be in a live, live attenuated or inactivated form.

The invention provides in a further aspect a vaccine for use in the protection of poultry against disease conditions resulting from an avian reovirus infection, such as enteric disease conditions observed with MAS, comprising an avian reovirus according to the invention and a pharmaceutical acceptable carrier or diluent.

The avian reovirus according to the present invention can be incorporated into the vaccine as a live attenuated or inactivated virus. The property of the avian reovirus to induce MAS-associated disease conditions as described above are significantly reduced or completely absent if the avian reovirus is in a live attenuated or inactivated form.

Attenuation of an avian reovirus according to the invention can be achieved by methods well known in the art for this purpose, such as disclosed in Gouvea et al. (Virology 126, 240–247, 1983). Briefly, after the isolation of the virus from a target animal, a virus suspension is inoculated onto primary chicken embryo fibroblasts (CEFs). If the isolate is not able to produce CPE, then the virus is passage repeatedly (e.g. 3–10 times) until CPE is observed. As soon as CPE is visible, cells and cell culture fluids are collected, frozen and thawed, clarified by centrifugation and the supernatant containing the avian reovirus isolate is aliquoted and stored at −20° C. This process may be repeated (e.g. 10–100 times) to further attenuate the virus.

A vaccine according to the invention can be prepared by conventional methods such as for example commonly used for the commercially available live—and inactivated reovirus vaccines. The preparation of veterinary vaccine compositions is inter alia described in "Handbuch der Schutzimpfungen in der Tiermedizin" (eds.: Mayr, A. et al., Verlag Paul Parey, Berline und Hamburg, Germany, 1984) and "Vaccines for Veterinary Applications" (ed.: Peters, A. R. et al., Butterworth-Heinermann Ltd, 1993).

Briefly, a susceptible substrate is inoculated with an avian reovirus according to the invention in a live or live attenuated form, and propagated until the virus replicated to a desired infectious titre or antigen mass content after which reovirus containing material is harvested and formulated to a pharmaceutical composition with prophylactic activity.

Every substrate which is able to support the replication of the avian reoviruses defined above, if necessary after adaptation of the avian reoviruses to a substrate, can be used to produce a vaccine according to the present invention. Suitable substrates include primary (avian) cell cultures, such as chicken embryo liver cells (CEL), chicken embryo fibroblasts (CEF) or chicken kidney cells (CK), mammalian cell lines such as the VERO cell line or the BGM-70 cell line, or avian cell lines such as QT-35, QM-7 or LMH. Usually, after inoculation of the cells, the virus is propagated for 3–10 days, after which the cell culture supernatant is harvested, and if desired filtered or centrifuged in order to remove cell debris.

Alternatively, the avian reovirus according to the invention can be propagated in embryonated chicken eggs followed by harvesting the avian reovirus material by routine methods.

The vaccine according to the invention containing the live attenuated virus can be prepared and marketed in the form of a (frozen) suspension or in a lyophilised form. The vaccine additionally contains a pharmaceutically acceptable carrier or diluent customary used for such compositions. Carriers include stabilisiers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below for the preparation of inactivated vaccines.

Although administration by injection, e.g. intramuscular, subcutaneous of the live vaccine according to the present invention is possible, the live vaccine is preferably administered by the inexpensive mass application techniques commonly used for avian reovirus vaccination. These techniques include drinking water and spray vaccination.

Alternative methods for the administration of the live vaccine include in ovo, eye drop and beak dipping administration.

In a preferred embodiment the present invention provides a vaccine against enteric disease conditions, such as those observed with MAS, comprising the avian reovirus in an inactivated form. The major advantage of an inactivated vaccine is the elevated levels of protective antibodies of long duration that can be obtained. This property makes such an inactivated vaccine in particular suited for breeder vaccination.

The aim of inactivation of the viruses after the propagation step is to eliminate reproduction of the viruses. In general, this can be achieved by chemical or physical means. Chemical inactivation can be effected by treating the viruses with, for example, enzymes, formaldehyde, $\beta$-propiolactone, ethylene-imine or a derivative thereof. If necessary, the inactivating compound is neutralised afterwards. Material inactivated with formaldehyde can, for example, be neutralised with thiosulphate. Physical inactivation can preferably be carried out by subjecting the viruses to energy-rich radiation, such as UV light or $\gamma$-rays. If desired, after treatment the pH can be adjusted to a value of about 7.

A vaccine containing the inactivated avian reovirus can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F° or Marcol 52® or a vegetable oil such as vitamin E acetate, and saponins.

Inactivated vaccines are usually administered parenterally, e.g. intramuscularly or subcutaneously.

The vaccine according to the invention comprises an effective dosage of the avian reovirus as the active component, i.e. an amount of immunising avian reovirus material that will induce immunity in the vaccinated birds or their progeny against challenge by a virulent virus. Immunity is defined herein as the induction of a significant higher level of protection in a population of birds after vaccination compared to an unvaccinated group.

Typically, the live vaccine according to the invention can be administered in a dose of $10^2-10^9$ TCID$_{50}$ per bird, preferably in a dose ranging from $10^2-10^6$ TCID$_{50}$, and an inactivated vaccine may contain the antigenic equivalent of $10^4-10^{10}$ TCID$_{50}$ per bird.

Although, the avian reovirus vaccine according to the present invention may be used effectively in chickens, also other poultry such as turkeys, guinea fowl and quail may be successfully vaccinated with the vaccine. Chickens include broilers, reproduction stock and laying stock.

Because enteric disease conditions, such as those observed with MAS hve been reported primarily in broiler chickens, the present invention preferably provides a vaccine for use in the protection of broilers against enteric disease conditions, such as those observed with MAS.

The age of the animals receiving a live or inactivated vaccine according to the invention is the same as that of the animals receiving the presently commercially available live- or inactivated avian reovirus vaccines. For example, broilers may be vacined directly from one-day-old onwards with the live attenuated vaccine according to the invention. Vaccination of parent stock, such as broilers breeders, can be done with a live attenuated or inactivated vaccine according to the invention or combinations of both. The advantages of this type of immunisation programme includes the immediate protection of one-day-old progeny provided by maternally derived antibodies vertically transmitted to the young birds. A typical breeder vaccination programme includes the vaccination of the breeders at 6-weeks of age with a live attenuated vaccine, followed by a vaccination between 14–18 weeks of age with an inactivated vaccine. Alternatively, the live vaccination may be followed by two vaccinations with inactivated vaccines on 10–12 weeks and 16–18 weeks of age.

The invention also includes combination vaccines comprising, in addition to the avian reovirus according to the invention, one or more vaccine components of other pathogens infectious to poultry. With such other pathogens infectious to poultry also avian reoviruses are meant which are antigenically distinct from the avian reoviruses according to the present invention, and include the avian reovirus strains associated with tenosynovitis.

Preferably, the vaccine components in the combination vaccine are the live attenuated or inactivated forms of the pathogens infectious to poultry.

In particular, the present invention provides a combination vaccine wherein all of the vaccine components are in an inactivated form.

Preferably, the combination vaccine comprises one or more (inactivated) vaccine strains of infectious bronchitis virus (IBV), Newcastle disease virus (NDV), infectious bursal disease virus (IBDV), fowl adenovirus (FAV), EDS virus and turkey rhinotracheitis virus (TRTV).

In the framework of the present invention the following microorganism and hybridoma cell lines have been deposited at the European Collection of Animal Cell Cultures (ECACC), Salisbury, UK on Jan. 14, 1999:

| virus/hybridoma | accession no. |
| --- | --- |
| avian reovirus ERS | 99011475 |
| INT13-06 | 99011472 |
| INT14-11 | 99011473 |
| 15-01 INT | 99011474 |

EXAMPLES

Example 1

Characterisation of the Novel Avian reoviruses

A
Isolation of the Novel Avian Reoviruses.

Intestine and/or liver were individually isolated from chickens having digestive problems and wet litter resulting in growth retardation. The organs were individually homogenised in a homogeniser using glass pearls (2 mm) and PBS with antibiotics, for 20 min at maximum speed. Thereafter, the homogenised tissues were centrifuged. Intestine homogenate was centrifuged at 4000 rpm, and liver was centrifuged at 1200 rpm both for 15 minutes. Next, the supernatants were filtered by pressing through filters with decreasing pore size (5, 1.2, 0.45, 0.2-$\mu$m). One hundred $\mu$l of suspension passing through the 0.2-$\mu$m fitler was added to freshly prepared primary chicken embryo liver (CEL) cells present in tissue culture flasks. Four to 8 days after incubation the monolayers were inspected for the presence of a cytopathic effect (CPE). If no CPE was present the monolayers were frozen at $-20°$ C., after 24 h the monolayers were thawed. Next, 1 ml of this freeze/thawed suspension was added to freshly prepared CEL cells. If no CPE was visible after 4–8 days the culture was considered negative for virus growing on CEL cells. If after the first passage or the second passage CPE was observed, then the virus was further characterised by the plaque reduction assay and immunofluorescence techique (IFT).

B
In Vitro Characterisation of the Novel Avian Reoviruses with the Plaque Reduction Assay
1. Production of Antiserum against different Avian Reovirus Strains
Strain ERS (live):

Ten, 3 weeks old SPF chickens were subcutaneously infected with $10^{5.8}$ TCID50/animal of strain ERS (isolate-2). Three weeks after infection blood was collected and serum isolated and animals were again infected $10^{5.6}$ TCID50/animal. Two weeks after the second infection blood was collected and serum isolated. After acquisition, all sera were heat inactivated 56° C., 30 min and stored in small aliquots at −20° C.

Strain 2177 (live):

Fifteen, 4 weeks old SPF chickens were subcutaneously infected with $10^{4.2}$ TCID50/animal. Four weeks after infection blood was collected and serum isolated. After acquisition, all sera were heat inactivated 56° C., 30 min and stored in small aliquots at −20° C.

Strains 1733 and 2408 (inac):

Twelve, 4 weeks old SPT chickens were intramuscularly inoculated with one of the avian reovirus strains 1733 or 2408 adjuvated with a w/o-emulsion. Animal dose: 490 Elisa Units/animal; representing an infectivity titre before inactivation between $10^{7.0}$–$10^{10.0}$ TCID50/animal. Four weeks after infection blood was collected and serum isolated. After acquisition, all sera were heat inactivated 56° C., 30 min and stored in small aliquots at −20° C.

Inactivate Commercially Available Vaccines Containing Avian Reovirus Strains:

Ten, 3–4 weeks old SPF chickens were intrasmuscularly or subcutaneously inoculated with one of the following commercially available inactivated avian reovirus vaccines: ISBI, Fort Dodge; Kaketsuken and Intervet International BV. Three weeks after infection blood was collected and serum isolated. After acquisition, all sera were heat inactivated 56° C., 30 min and stored in small aliquots at −20° C.

The sera prepared above were used in the IFT and plague reduction assay.

2. Immunofluorescence Test (IFT)

The IFT is carried out essentially as described in paragraph C. below, Briefly, Vero cells were grown in 96-well polystyrene microtitre plates until confluence. Different monolayers were inoculated with Reovirus strain 1133. 100 $\mu$l of chicken serum was added to the first well of the plate. Serial 3-fold dilutions are made. After the incubation and washing steps, the plates were reacted with 1:100 diluted fluorescent isothiocyanate-labelled goat-anti-chicken. The presence of fluorescence was observed with a fluorescence microscope. The titre (quality of the serum) is determined by end point dilution. This is the highest dilution of serum that is still able to induce a clear fluorescence signal. In Table 1 the results of the IFT for sera used in the plaque reduction test are shown:

TABLE 1

| Serum against avian reovirus strain | End dilution (expressed in log2) |
| --- | --- |
| 2177 | 2025 (11.0) |
| ERS | 6075 (12.6) |
| 1733 | 6075 (12.6) |
| 2408 | 18225 (14.2) |
| Arvax | 75 (6.2) |
| Nobilis Reo | 18225 (14.2) |
| Tri Reo | 6075 (11.6) |
| Oilvax Reo | 18225 (14.2) |
| Negative serum | <3 (<1) |

Nobilis Reo™ commercially available from Intervet International b.v.
Arvax™ commercially available from ISBI
TriReo™ commercially available from Fort Dodge
Oilvax Reo™ commercially available from Katetsuken 3. Plaque Reduction Assay Antiserum of appropriate quality should be used in the plaque reduction assay to determine the antigenic relationship between avian reviruses belonging to the new antigenic class and to distinguish the new avian reoviruses from known avian reoviruses (all but the Arvax antiserum fulfilled the required quality of the antiserum). ERS antiserum was raised against live ERS isolate 1, and live and inactivated ERS isolate 2. Freshly prepared CELs were resuspended in tissue culture medium supplemented with 5% fetal calf serum and antibiotics to a final concentration of 1 $10^6$ cells per millilitre. Sixty-mm tissue culture dishes were filled with 5 -ml cell suspension and incubated at 37° C. for 24 h.

The next day the virus to be investigated were diluted in plastic tubes in medium with antibiotics. Dilutions from $10^{-1}$ till $10^{-7}$ were prepared. Next 200 $\mu$l of each dilution was mixed with 50 $\mu$l of the serum to be tested. This mixture was incubated at 37° C. for 1 h. As negative control 200 $\mu$l of virus dilution was mixed with 50 $\mu$l of medium.

The medium on top of the monolayers present in the 60-mm tissue culture dishes was discarded. Next, 100 $\mu$l of the different virus mixtures (with or without serum) is added onto a confluent monolayer. For each virus mixture at least 2 monolayers (dishes) were infected. The infected monolayers were incubated for 1 h at 37° C. Thereafter, the infected monolayers were covered with 5 ml agar-solution (containing medium, FCS and antibiotics; final agar concentration 3.0%; final FCS concentration 2.5%). The dishes were incubated for 4 days at 37° C. Next to each tissue culture dish 2-ml neutral red solution (0.025) was added. After 4 h of incubation at 37° C. the number of plaques were counted per dish. Only the tissue culture dishes that contained 150 or less plaques were counted.

Plaque reduction is calculated as follows: the number of plaques of a certain virus at a certain dilution without serum is set at 100%. This is then compared to the number of plaques at the same virus dilution but with serum.

The results of a first experiment with different viruses and sera tested are given in Table 2A. Table 2B shows the result of a second experiment with the viruses and sera as indicated. The serum against the inactivated ERS vaccine was raised as described for the inactivated 1733/2408 strains, except that blood was collected 5 weeks after vaccination.

reacted with 1:100 diluted fluorescent isothiocyanate-labelled rabbit-antimouse- or 1:100 diluted isothiocyanate-labelled goat-anti-rabbit serum. Finally, the plates were washed and fixed with a glycerol/PBS solution (1:1). The Presence of Fluroescence was observed with a Fluorescence Microscope.

The antiserum panel used in this experiment consisted of the following polyclonal antiserum and Moabs raised against the prototype avian reovirus strain 1133:
Rabbit 68A rabbit polyclonal antiserum
Moab 154 Vakharia et al. 1996 (supra)
Moab 14-67 Intervet International B. V.
Moab INT 13-06 ECACC accession no. 99011472
Moab INT 14-11 ECACC accession no. 99011473
Moab 15-01 INT ECACC accession no. 99011474
Avian reovirus isolates obtained by the method described above were further characterised by their reactivity with this antiserum panel. The new reovirus isolates have a distinct reaction pattern with the panel of poly- and monoclonal antibodies. The hitherto known avian reovirus strains

TABLE 2A

| Virus | Serum | | | | | | | | |
|---|---|---|---|---|---|---|---|---|---|
| | 1733 inac | 2408 inac | 2177 live | ERS-2 live | Nobilis Reo inac | Arvax inac | Tri Reo inac | Oilvax Reo inac | neg – |
| ERS-1 | 0* | 0 | 0 | 89 | | | | | – |
| ERS-2 | 0 | 0 | 0 | 91 | 0 | 0 | 0 | 0 | – |
| ERS-3 | 0 | | | 100 | | | | | – |
| 1733 | 91 | | | 85 | | | | | – |
| 2408 | | 91 | | 87 | | | | | – |
| 2177 | | | 85 | 83 | | | | | – |
| K255 | 91 | | 88 | 98 | | | | | – |

*% plaque reduction
– reference

TABLE 2B

| Virus | Serum | | | |
|---|---|---|---|---|
| | ERS-2 live | ERS-1 live | inactivated ERS vaccine | 1133 live |
| ERS-2 | 95* | 81 | 89 | 12 |
| ERS-1 | 100 | 100 | nd | nd |

*% plaque reduction
nd = not done

C
In Vitro Characterisation of the Novel Avian Reoviruses with IFT: Antiserum Panel Reaction Pattern Polyclonal antiserum was prepared by infecting rabbits (1–1,5 kg) with purified avian reovirus strain 1133. Booster injections took place 28 and 84 days after the first infection. Blood was collected and serum isolated 14 days after the last injection. The different avian reovirus strains were characterised with different Moabs. Primary CEL cells were grown in 96-well polystyrene microtitre plates. Uninfected cells served as controls. After 2–4 days of incubation at 37° C. with 5% CO2, infected monolayers were fixed with cold 96% ethanol. The alcohol was discarded and the plates were washed with washing buffer and 100 μl of different hybridoma cell culture supernatant diluted 1:50 or 1:200 in PBS or 100 μl of rabbit polyclonal serum (rabbit 68A) diluted 1:50, was added to each well. The plates were incubated for 60–90 min at 37° C., washed twice with washing buffer and (S-1133 to CO8) isolated from field cases of MAS and tenosynovitis do not react according to the new pattern (see Table 3).

New Reaction Pattern Positive: polyclonal rabbit 68A, 154, 14-67 Negative: INT 13-06, INT 14-11, 15-01 INT

TABLE 3

| Virus | Rabbit 68A | 154 | 14-67 | INT 14-11 | INT 13-06 | 15-01 INT |
|---|---|---|---|---|---|---|
| S-1133 | | | | | | |
| 1133 | | | | | | |
| 2408 | | | | | | |
| UM 203 | | | | | | |
| WVU 1675 Olson | | | | | | |
| 6261 | | | | | | |
| Enterovax™ | | | | | | |
| Tensynovac™ | | | | | | |
| 1733 | | | | | | – |
| 2177 | | | | – | – | |
| 206691 | | | | – | – | |
| CO8 | | | | | – | |

TABLE 3-continued

| ERS isolates | | | | | | |
|---|---|---|---|---|---|---|
| ERS-1 | + | + | + | - | - | - |
| ERS-2 | + | + | + | - | - | - |
| ERS-3 | + | + | + | - | - | - |
| ERS-4 | + | + | + | - | - | - |
| ERS-5 | + | + | + | - | - | - |
| ERS-6 | + | + | + | - | - | - |
| ERS-7 | + | + | + | - | - | - |
| ERS-8 | + | + | + | - | - | - |
| ERS-9 | + | + | + | - | - | - |
| ERS-10 | + | + | + | - | - | - |
| ERS-11 | + | + | + | - | - | - |
| ERS-12 | + | + | + | - | - | - |
| ERS-13 | + | + | + | - | - | - |

Enterovax ™ and Tensynovac ™ are avian reovirus vaccines commercially available from Schering-Plough Animal Health and Intervet Inc.

D

Figure 2A:
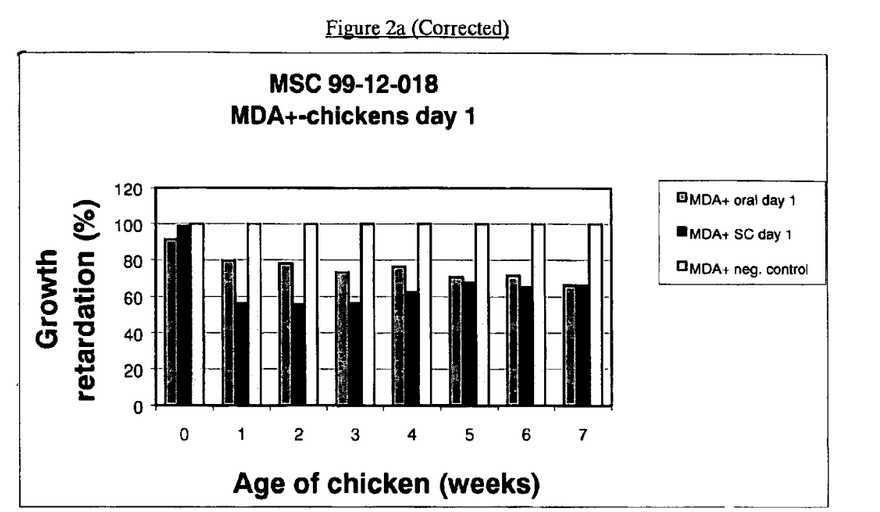
FIG. 2A illustrates growth retardation of broilers infected with ERS at one day of age.
Figure 2B:
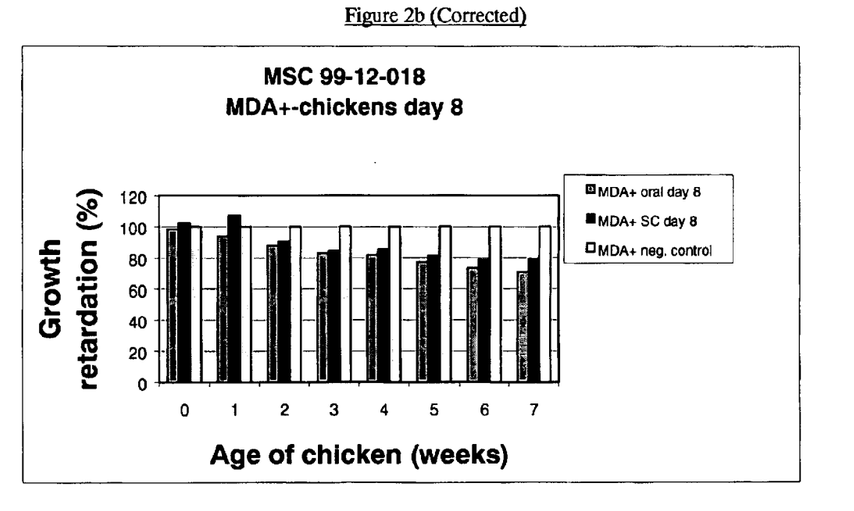
FIG. 2B illustrates growth retardation of broilers infected with ERS at eight days of age.

In Vivo Characterisation of the Novel Avian Reoviruses
Experimental Infection with Plaque Purified Avian Reovirus ERS
Experiment 1
30 one-day-old SPF chickens were orally infected with plaque purified reovirus ERS (isolate 1). Four, 7 and 10 days after infection livers from 10 animals were isolated and investigated for microscopic lesions.
Experiment 2
30 one-day old broilers with maternal antibodies against reovirus were orally infected with plaque purified reovirus strain ERS. Seven and 10 days infection animals were observed for clinical signs. Special attention was paid to wet litter
Experiment 3
30 one-day-old broilers with maternal antibodies against reovirus were orally infected with plaque purified reovirus strain ERS. One, 2 and 4 weeks after infection 10 animals per group were weighted to investigate growth retardation.
Experiment 4
Fifteen, one-day-old broilers with maternal antibodies against reovirus per group were orally or subcutaneously infected with plaque reovirus strain ERS (isolate-2), at day old or at 1 week old. Fifteen animals of the same age and source were not infected and served as negative control. Animals were weighed each week for a period of 7 weeks to investigate growth retardation.
Results
Experiment 1
One-day-old infected SPF chickens that were orally infected with the reovirus showed multifocal vacuolation of hepatocytes and/or Kupffer cells, 4 to 10 days after infection.
Experiment 2
Ten days after oral infection, broilers showed enteritis resulting in too liquid faeces observable as clothing of pasting around the cloaca of the birds in contrast to a non-infected broiler control group of the same age and source held under identical conditions.
Experiment 3
One-day-old orally infected broilers had a weight of 121.9, 327.0 or 913.1 g. at the age of 1, 2 or 4 weeks old. In contrast, non-infected broilers of the same age and source housed under identical conditions weighed 134.8, 337.6 or 999.9 g., at the age of 1, 2 or 4 weeks old.
Experiment 4
Results are depicted in FIGS 2A and 2B. At the age of 7 weeks animals infected at day old via the oral or subcutaneous route showed a growth retardation of approximately 34% compared to the non-infected control animals. At 7 weeks of age, the ratio in weight between non-infected controls animals versus infected animals was 2469 g versus 1635 g.
At the age of 7 weeks animals infected at one week old via the oral or subcutaneous route showed a growth retardation of approximately 25% compared to the non-infected control animals. At 7 weeks of age, the ratio in weight between non-infected control animals versus infected animals was 2469 g versus 1842 g.
In conclusion, the reovirus strain ERS is capable of inducing growth retardation.

Example 2

Animal Vaccination Studies

Figure 1A:
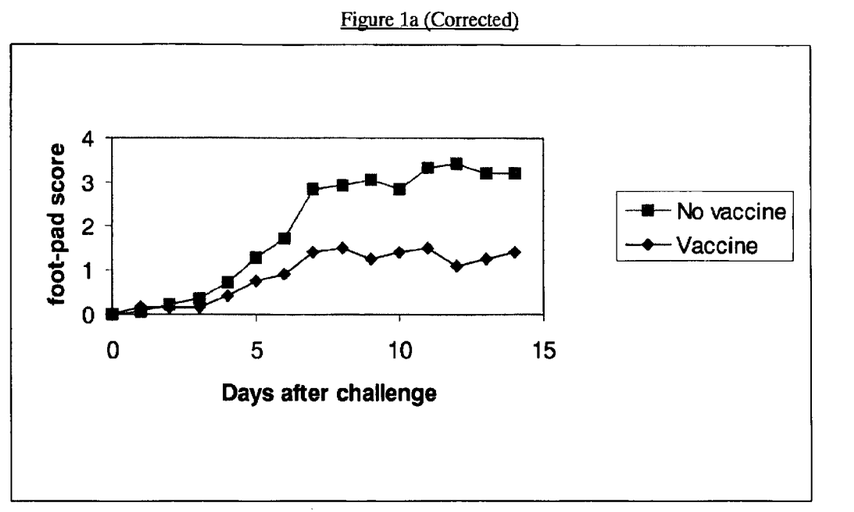
FIG. 1A illustrates the protection obtained evaluated by footpad lesions.
Figure 1B:
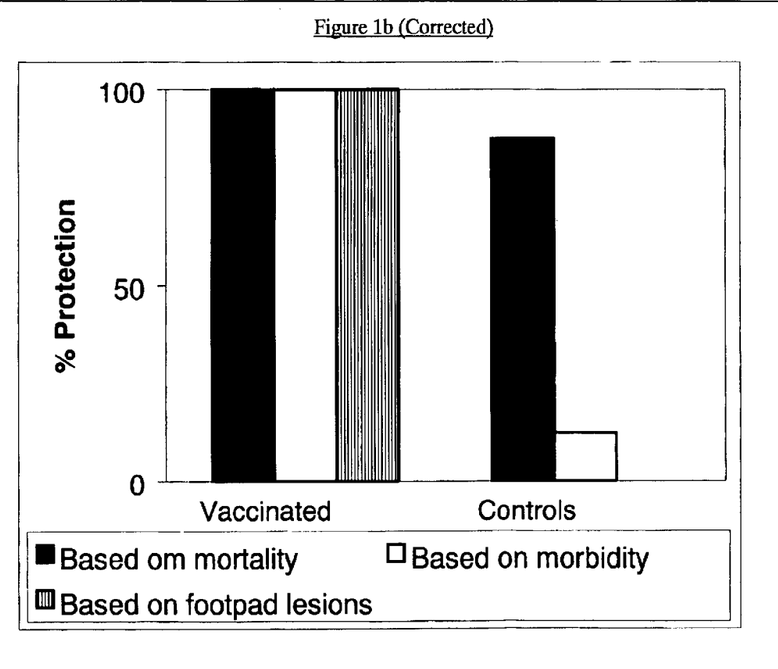
FIG. 1B illustrates the protection obtained evaluated by mortality, morbidity and footpad lesions.

A
Preparation of an Inactivated Avian Reovirus Vaccine
Primary CEL cells were prepared at a final concentration of $1 \times 10^6$ cells/ml. The cells were cultured in Eagles MEM containing 0.1% antibiotics and 5% foetal calf serum. To 25 ml of this cell suspension 0.1 ml of reovirus isolate ERS (isolate 1) was added. After incubation for 5 days in a high-humidity incubator at 37° C., CPE was clearly visible and the monolayer completely destroyed. The infectious titre of the infected cell suspension was 4.2 log10 $TCID_{50}$/ml. The reovirus was inactivated by adding formaldehyde to the infected cell suspension to an end concentration of 0.2%. The suspension was incubated at 37° C. for 48 h.
Thereafter, the formaldehyde was neutralised by an equimolar amount of sodiumbisulfiet. The inactivated reovirus was used to prepare different inactivated reovirus vaccines. The inactivated reovirus suspension was mixed with a mineral oil phase in a ratio of 45:55 (w/o emulsion).
Vaccination
SPF animals of 3–4 weeks old were intramuscularly vaccinated with the inactivated reovirus vaccines (0.5 ml/animal). Two, 4 and 6 weeks after vaccination serum was investigated for the presence of antibodies against reovirus. Six weeks after vaccination animals were challenged via the footpad route. Challenge virus used was the pathogenic homologous reovirus strain (2.2 log $TCID_{50}$/animal). The degree of inflammation and discoloration of the footpad and shank was scored for a period of 2 weeks. A chicken was considered protective against challenge if the footpad inflammation cumulative value was less than the mean of the footpad inflammation of the non-vaccinated challenged controls minus two standard deviations.
In a similar study as outline above, the animals were challenged at five weeks of age and the protection against severe challenge was evaluated by means of mortality, morbidity and footpad lesions
Results
The protection data are depicted in FIGS. 1A and 1B. The vaccinated chickens showed a footpad inflammation cumulative value which is significantly reduced compared to the control group, indicating that the vaccinated chickens were protected against severe reovirus challenge. The protection data based on mortality and morbidity also demonstrate a significant protection against sever challenge.

B
Vaccination
SPF animals of 3–4 weeks old were intramuscularly vaccinated with inactivated ERS reovirus vaccine (isolate 2) similar to that described above and revaccinated 6 weeks after the first vaccination. Not vaccinated animals of the same age and source served as control. Two, 4, 5, 6 weeks after the first vaccination and 2 weeks after the second vaccination sera were investigated for the presence of antibodies against Reovirus with the Idexx ELISA. Six weeks after the first vaccination or 2 weeks after the second vaccination animals were challenged via the footpad route with pathogenic Reovirus strain ERS. The average lesion score of the degree of inflammation and discoloration of the footpad and shank was measured each day for a period of 14 days after challenge.

Results

Figure 3A:
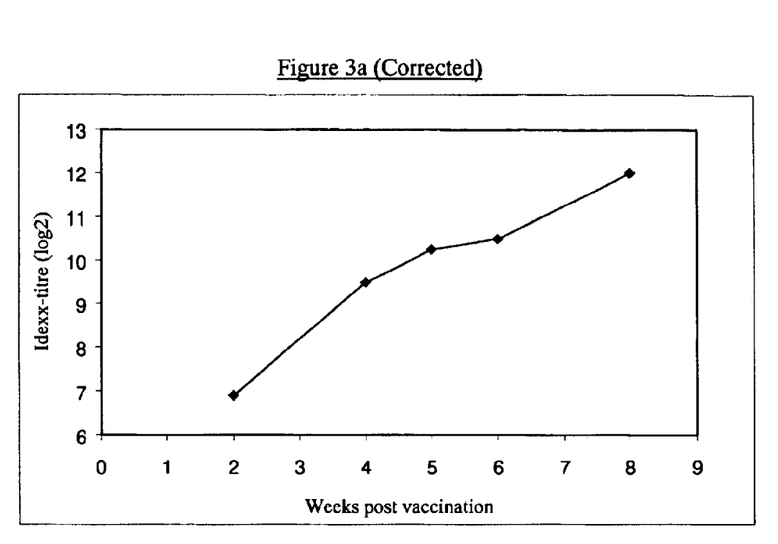
FIG. 3A illustrates the serological response after vaccination.
Figure 3B:
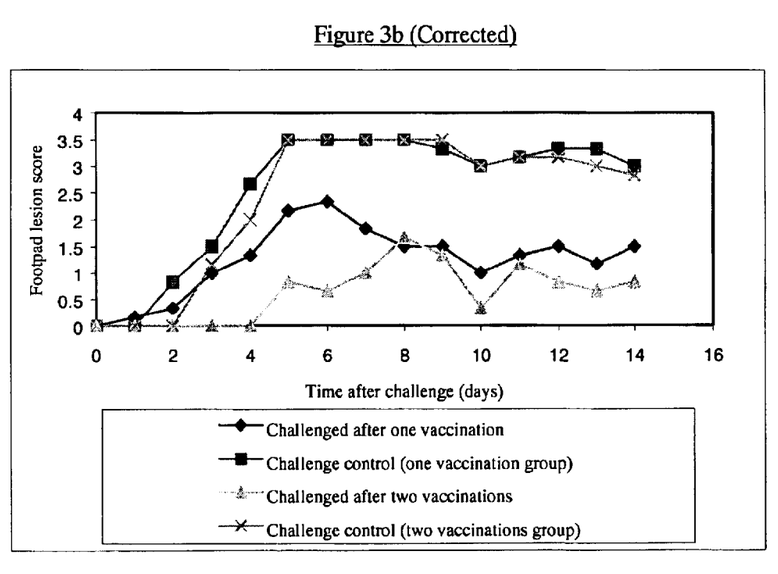
FIG. 3B illustrates the footpad lesion score on challenge after vaccination.

The serological response induced by the inactivated reovirus ERS vaccine increased in the first 4 weeks after vaccination and levelled off between 5 and 6 weeks after the first vaccination. The second vaccination results in an increase from approximately 10 log2 to 12 log2, 2 weeks after the second vaccination (FIG. 3A). In FIG. 3B the data are shown of vaccinated and non-vaccinated chickens that were challenged 5 weeks after the first vaccination or 2 weeks after the second vaccination. All vaccinated chickens showed a significant decrease of lesions in the footpad and shank compared to non-vaccinated birds. All vaccinated chickens showed footpad inflammation cumulative values less than the mean of the footpad inflammation of the non-vaccinated, challenge controls minus two standard deviations, indicating that all animals were protected against severe REO challenge. Some mild footpad swellings were observed in the vaccinated group, however these lesions were of a temporary nature. Furthermore, the temporary footpad lesions were less in the animals that were vaccinated twice when compared to animals that were vaccinated once.

I claim:

1. A vaccine comprising an isolated avian reovirus belonging to an antigenic class of avian ERS reoviruses wherein the avian reovirus is able to induce antiserum in an animal, which causes a reduction of the plaques formed by avian reovirus ERS(isolate 1), deposited at the ECACC under accession no. 99011475, of at least 75% in a plaque reduction assay and wherein the avian reovirus positively reacts with polyclonal avian reovirus antiserum raised against strain 1133, but not with monoclonal antibodies identified by accessions nos. 99011472, 99011473 and 99011474, samples of which are deposited at the ECAC, and a pharmaceutical acceptable carrier or diluent.

2. The vaccine according to claim 1, which is in a live attenuated form.

3. The vaccine according to claim 1, which is in an inactivated form.

4. The vaccine according to claim 1, which further comprises an adjuvant.

5. The vaccine according to claim 1, which further comprises one or more vaccine components of other pathogens infections to poultry.

6. A vaccine comprising an avian reovirus which is avian reovirus ERS, a sample of which is deposited at the ECACC under accession no. 99011475, and a pharmaceutically acceptable carrier or diluent.

7. The vaccine of claim 5 wherein the one or more vaccine components comprises at least one vaccine component selected from the group consisting of infectious bronchitis virus, Newcastle disease virus, infectious bursal disease virus, fowl adenovirus, EDS virus and turkey rhinotracheitis virus.

8. The vaccine of claim 5 wherein the one or more vaccine components are either one of a live attenuated form or an inactivated form.

9. The vaccine of claim 1 wherein the avian reovirus is able to induce antiserum in an animal, which antiserum causes a reduction of the plaques formed by avian reovirus ERS, a sample of which is deposited at the ECACC under accession no. 99011475, of at least 80% in a plaque reduction assay.

10. The vaccine of claim 1 wherein the avian reovirus is able to induce antiserum in an animal, which anitserum causes a reduction of the plaques formed by avian reovirus ERS, a sample of which is deposited at the ECACC under accession no. 99011475, of at least 90% in a plaque reduction assay.

* * * * *